US010132736B2

(12) United States Patent
Matayoshi et al.

(10) Patent No.: US 10,132,736 B2
(45) Date of Patent: Nov. 20, 2018

(54) METHODS FOR INSPECTION OF PROTEIN PARTICLES IN A LIQUID BENEFICIAL AGENT

(71) Applicant: AbbVie Inc., North Chicago, IL (US)

(72) Inventors: Edmund Matayoshi, Richmond, IL (US); Jie Wang, Lake Bluff, IL (US)

(73) Assignee: ABBVIE INC., North Chicago, IL (US)

( * ) Notice: Subject to any disclaimer, the term of this patent is extended or adjusted under 35 U.S.C. 154(b) by 494 days.

(21) Appl. No.: 13/841,143

(22) Filed: Mar. 15, 2013

(65) Prior Publication Data
US 2013/0316934 A1 Nov. 28, 2013

Related U.S. Application Data

(60) Provisional application No. 61/651,211, filed on May 24, 2012.

(51) Int. Cl.
G01N 15/14 (2006.01)
G01N 33/15 (2006.01)
G01N 15/06 (2006.01)
G01N 21/51 (2006.01)
G01N 21/90 (2006.01)
G01N 21/64 (2006.01)
C07K 16/24 (2006.01)

(52) U.S. Cl.
CPC ....... G01N 15/1434 (2013.01); C07K 16/241 (2013.01); G01N 15/06 (2013.01); G01N 21/51 (2013.01); G01N 21/6456 (2013.01); G01N 21/9027 (2013.01); G01N 33/15 (2013.01); G01N 2015/0693 (2013.01)

(58) Field of Classification Search
None
See application file for complete search history.

(56) References Cited

U.S. PATENT DOCUMENTS

| | | | |
|---|---|---|---|
| 3,627,423 A | 12/1971 | Knapp et al. |
| 3,713,743 A | 1/1973 | Simms |
| 3,830,969 A | 8/1974 | Hofstein |
| 4,028,553 A | 6/1977 | Farcinade |
| 4,814,868 A | 3/1989 | James |
| 4,893,320 A | 1/1990 | Yanagi et al. |
| 5,269,937 A | 12/1993 | Dollinger et al. |
| 5,835,211 A | 11/1998 | Wells et al. |
| 2010/0102247 A1 | 4/2010 | Arvinte |

FOREIGN PATENT DOCUMENTS

| | | |
|---|---|---|
| CN | 101583863 A | 11/2009 |
| CN | 103003688 A | 3/2013 |
| EP | 0 926 482 | 6/1999 |
| JP | H 03-156370 A | 7/1991 |
| JP | H 11-183382 A | 7/1999 |
| JP | 2009-530380 A | 8/2009 |
| JP | 2011-252804 A | 12/2011 |
| JP | 2014-528560 | 9/2014 |
| WO | WO 2007/109221 A2 | 9/2007 |
| WO | WO 2009/073649 | 11/2009 |
| WO | WO 2011/056590 A1 | 5/2011 |
| WO | WO 2012/016159 | 2/2012 |
| WO | WO 2013/033253 A1 | 3/2013 |

OTHER PUBLICATIONS

Koller, "A high-throughput alphavirus-based expression cloning system for mammalian cells," Nature biotechnology, vol. 19, p. 851-855, 2001.*
Merkus, "Particle Size Measurements," Particle Technology Series, chapters 1-20, 535 pages, Springer, Netherlands, 2009.*
Debye, "Molecular-weight determination by light scattering," The Journal of Physical Chemistry, vol. 51(1), p. 18-32, 1947.*
International Search Report for PCT/US2013/042481, dated Dec. 6, 2013.
U.S. Appl. No. 14/691,322 (US 2015/0226659), filed Apr. 20, 2015 (Aug. 13, 2015).
Demeule et al., "New methods allowing the detection of protein aggregates" MAbs, Mar. 1/Apr. 2009, vol. 1, No. 2, pp. 142-150.
Search Report and Written Opinion dated Sep. 28, 2015 in Singapore Patent Application No. 11201407660S.
CN Office Action dated Jan. 19, 2016 in CN Patent Application No. 201380039409.8 (with English translation).
U.S. Appl. No. 14/691,322, filed Jun. 8, 2017 Response to Non-Final Office Action.
U.S. Appl. No. 14/691,322, filed Apr. 24, 2017 Applicant Initiated Interview Summary.
U.S. Appl. No. 14/691,322, filed Mar. 9, 2017 Non-Final Office Action.
U.S. Appl. No. 14/691,322, filed Nov. 30, 2016 Supplemental Response/ Amendment.
U.S. Appl. No. 14/691,322, filed Oct. 28, 2016 Applicant Initiated Interview Summary.
U.S. Appl. No. 14/691,322, filed Oct. 5, 2016 Amendment and Request for Continued Examination (RCE).
U.S. Appl. No. 14/691,322, filed Sep. 2, 2016 Advisory Action.
U.S. Appl. No. 14/691,322, filed Aug. 23, 2016 Response after Final Office Action.

(Continued)

Primary Examiner — G Steven Vanni
(74) Attorney, Agent, or Firm — Baker Botts L.L.P.

(57) ABSTRACT

Detection of particles in a liquid beneficial agent contained within a container includes selectively illuminating at least a portion of the liquid beneficial, obtaining an image from the illuminated portion of the liquid beneficial agent, analyzing image data representing the image, using a data processor, to obtain a particle concentration, measuring an image intensity value of the image data using the data processor, and determining a quality level of the liquid beneficial agent using the data processor based on the particle concentration and the measured image intensity value.

16 Claims, 15 Drawing Sheets

(56) References Cited

OTHER PUBLICATIONS

U.S. Appl. No. 14/691,322, filed Jul. 5, 2016 Final Office Action.
U.S. Appl. No. 14/691,322, filed Apr. 13, 2016 Response to Non-Final Office Action.
U.S. Appl. No. 14/691,322, filed Jan. 13, 2016 Non-Final Office Action.
U.S. Appl. No. 14/691,322, filed Nov. 25, 2015 Response to Restriction Requirement.
U.S. Appl. No. 14/691,322, filed Nov. 24, 2015 Applicant Initiated Interview Summary.
U.S. Appl. No. 14/691,322, filed Sep. 25, 2015 Restriction Requirement.

* cited by examiner

METHODS FOR INSPECTION OF PROTEIN PARTICLES IN A LIQUID BENEFICIAL AGENT

CROSS-REFERENCE TO RELATED APPLICATIONS

This application claims the benefit of U.S. Provisional Application No. 61/651,211, filed May 24, 2012, which is incorporated by reference herein in its entirety.

BACKGROUND

Field of the Disclosed Subject Matter

The present disclosed subject matter relates to systems and methods for detection of particles, such as protein monomers, protein aggregates and foreign particles, which can be found in a liquid beneficial agent.

Description of Related Art

Beneficial agents for diagnostic and therapeutic uses typically are available in liquid form. Such liquid beneficial agents can be biologics, small molecule pharmaceuticals, nutritional products, or combinations thereof. It is often helpful, if not necessary, to inspect such liquid beneficial agents to ensure particles, contaminants, aggregates, or other undesirable materials are not present. Preferably, such inspection occurs during manufacture and packaging. Additionally, however, such inspections may be helpful after shipping, during storage, and/or prior to use.

One of the most common routes of administration for liquid beneficial agents is by injection, including intravenous, subcutaneous or intramuscular injection. For example, a syringe containing the liquid beneficial agent can be used for the injection, which typically is carried out by medical personnel or other health care providers. In certain instances, a patient is trained in the use of the syringe to allow for self-injection. Moreover, certain medications are formulated in pre-filled syringes for patient use, to avoid the need for the patient to fill the syringe. Such pre-filled syringes can be packaged in an automatic injection device, which provides an easier-to-use and more rapid delivery system for the beneficial agent.

As noted, it can be helpful or necessary to inspect the contents of the pre-filled syringe to ensure quality and safety of the beneficial agent. For example, it is often desirable to inspect biological drugs for protein aggregates. When biological drugs are formulated at relatively high concentrations or volumes, the risk of generating molecular aggregates can increase. These aggregates can range in size from a few nanometers to many microns.

Naked eye inspection of the contents of a syringe is a recognized and generally acceptable method used for quality control. However, naked eye inspection can be subjective and can lack the sensitivity to detect low concentrations of particles or subvisible particles. Certain commercial systems have been developed with automated operation and relatively high sample throughput inspection of syringe contents for particles. Some commercially available systems, for example Seidenader VI series and Brevetti K15 systems, can provide high-throughput syringe inspection noninvasively, but can only effectively detect "visibles" (i.e., particles larger than about 10-25 microns). In contrast, some known experimental research lab systems can provide higher resolution particle detection, but these systems rely on manual and/or invasive techniques that render relatively low sample throughput. For example, dynamic light scattering (DLS) can provide a molecular resolution of about 1 nm, and Nanoparticle Tracking Analysis (NTA), used in systems marketed by NanoSight Ltd., can image particles as small as about 20 nm. However, these invasive techniques have a relatively low throughput compared to other methods.

U.S. Patent Application Publication No. 2010/0102247 to Arvinte describes a digital scanner-based particle detection technique for improved sensitivity over commercial systems. However, such a system can be limited by the resolution of the scanner and relatively low contrast, and thus can be ineffective at detecting low concentrations of subvisible particles (for example, below about 1 to 10 microns in size).

As such, there remains a need for systems and methods that can noninvasively provide high-throughput, high-sensitivity evaluation of liquid beneficial agents, particularly in pre-filled syringes, to detect the presence of sub-micron particles, even in low concentrations.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a method for detection of particles in a liquid beneficial agent contained within a container. The method includes selectively illuminating at least a portion of the liquid beneficial agent; obtaining an image from the illuminated portion of the liquid beneficial agent; analyzing image data representing the image, using a data processor, to obtain a particle concentration; measuring an image intensity value of the image data using the data processor; and determining a quality level of the liquid beneficial agent using the data processor based on the particle concentration and the measured image intensity value.

For example and as embodied herein, selectively illuminating a portion of the liquid beneficial agent can include focusing light through an optical element corresponding to the container to provide an undistorted image from the illuminated portion of liquid beneficial agent. Selectively illuminating the portion of the liquid beneficial agent can also include forming a thin sheet of illumination in the illuminated portion of the liquid beneficial agent. The liquid beneficial agent can be selectively illuminated with light having a wavelength in a range from about 200 nm to about 1100 nm.

In some embodiments, the image is obtained by or as a result of light scattering from the particles in the illuminated portion of the beneficial agent. Additionally or alternatively, the liquid beneficial agent can have intrinsic fluorescence, and the liquid beneficial agent can be selectively illuminated with light having an excitation wavelength suitable to cause the liquid beneficial agent to emit fluorescent light of an emission wavelength. Obtaining the image therefore can include using an optical filter corresponding to the emission wavelength of the emitted fluorescent light. Obtaining the image can also include focusing an image detector through an optical element corresponding to the container to provide an undistorted image from the liquid beneficial agent. Additionally or alternatively, obtaining the image can include the use of a difference image analysis technique, wherein a first image and a second image are captured from the illuminated portion of the liquid beneficial image, and then a difference image can be obtained from the first image and the second image to correct for interfering background.

Furthermore and as embodied herein, the method can include calibrating an image detector to a predetermined sensitivity. Analyzing the image data to obtain a particle concentration thus can be performed using a single image frame and include counting a number of particles exceeding a size threshold or an intensity threshold to determine a particle concentration and analyzing a particle intensity distribution. By contrast, measuring the image intensity value of the image data can include determining a pixel intensity value of each pixel of a plurality of pixels of the image data using the data processor and combining the pixel intensity values of the plurality of pixels to determine the image intensity value using the data processor. Determining the quality of the liquid beneficial agent thus can include comparing the particle concentration to a particle concentration threshold, as well as comparing the image intensity value to an image intensity threshold. The particle concentration threshold and the image intensity threshold can be obtained from a representative profile. The method can also include determining an average molecular mass of the particles using the image intensity value, wherein the quality level is further determined using the average molecular mass. The detection therefore can be performed on a plurality of containers in a high-throughput manner.

The disclosed subject matter also includes a system for detection of particles in a liquid beneficial agent within a container. The system includes a light source configured to illuminate at least a portion of the liquid beneficial agent, an image detector configured to obtain an image from the illuminated portion of the liquid beneficial agent, and a data processor coupled to the image detector. The data processor is programmed to analyze image data representing the image from the image detector to obtain a particle concentration; measure an image intensity value of the image data; and determine a quality level of the liquid beneficial agent based on the particle concentration threshold and the measured image intensity value. The system can include any or all of the features described herein.

The disclosed subject matter also includes a beneficial treatment product. The beneficial treatment product includes a container containing a liquid beneficial agent and a system for detection of particles in the liquid beneficial agent including any of the features described herein.

The disclosed subject matter also includes a liquid beneficial agent having a predetermined quality level, as determined by the method for detection described herein. For example, the liquid beneficial agent can include a protein. Particularly, the protein can be a fusion protein, and the liquid beneficial agent and can have a protein concentration between about 0.1 mg/ml and about 200 mg/ml. The protein can be an antibody, and the antibody can be an anti-Tumor Necrosis Factor alpha (TNFα) antibody, or antigen-binding fragment thereof.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the disclosed subject matter. Together with the description, the drawings serve to explain the principles of the disclosed subject matter.

DETAILED DESCRIPTION OF THE PREFERRED EMBODIMENT

Figure 1:
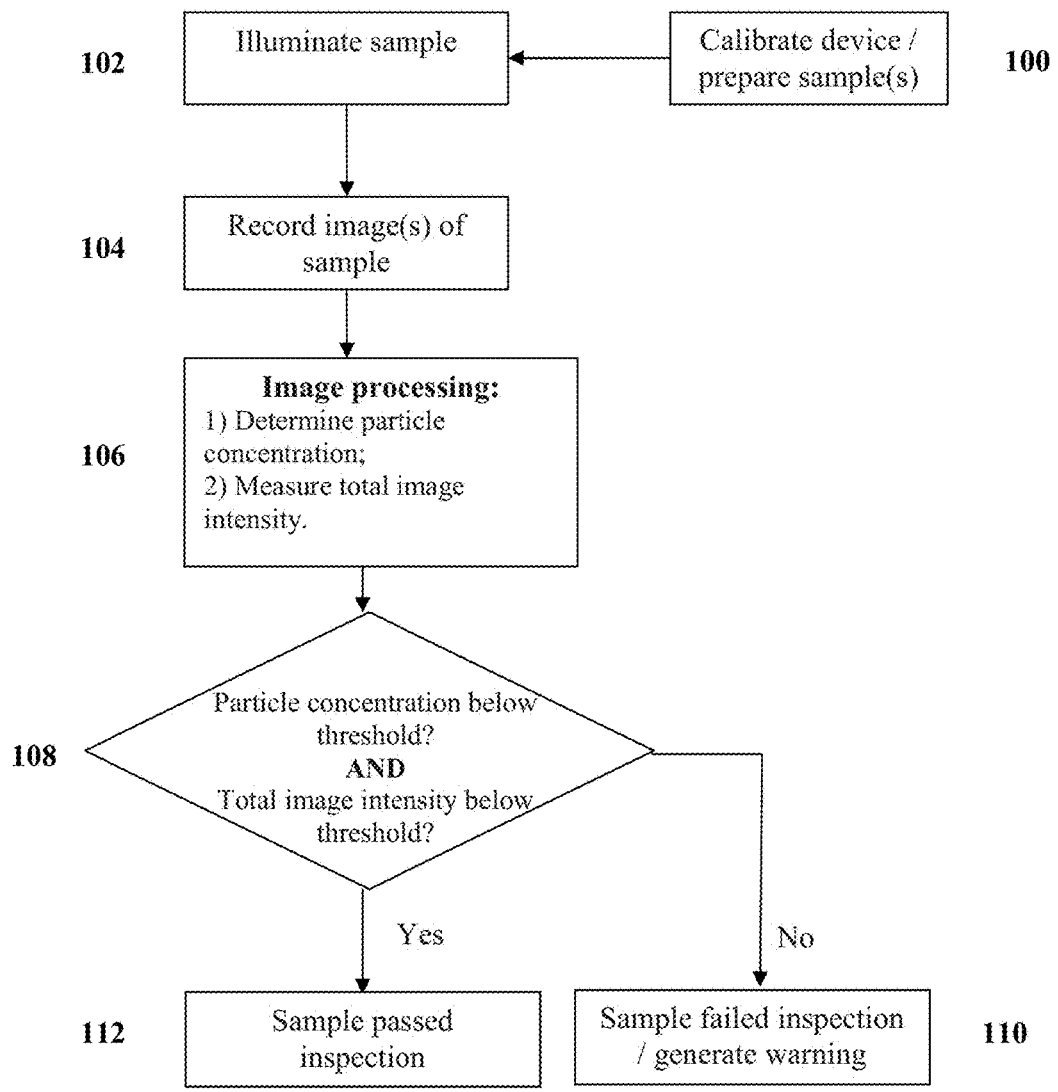
FIG. 1 is a diagram illustrating a representative method implemented according to an illustrative embodiment of the disclosed subject matter.

Reference will now be made in detail to the various exemplary embodiments of the disclosed subject matter, exemplary embodiments of which are illustrated in the accompanying drawings. The structure and corresponding method of operation of the disclosed subject matter will be described in conjunction with the detailed description of the system.

The systems and methods presented herein can be used for detection of particles, such as proteins and protein aggregates or any other visible or subvisible particles, in any of a variety of suitable beneficial agents or substances. As used herein, a "liquid beneficial agent" or "beneficial agent" (used interchangeably herein) is intended to refer generally to a substance or formulation in liquid form to be administered to or used by an individual (also referred to herein as a user or a patient) for an approved medical indication, such as a medication, diagnostic, nutritional, or other therapeutic agent.

In accordance with the disclosed subject matter herein, a method for detection of particles in a liquid beneficial agent contained within a container (also referred to herein as a "detection method") generally includes selectively illuminating at least a portion of the liquid beneficial agent; obtaining an image from the illuminated portion of the liquid beneficial agent; analyzing image data representing the image, using a data processor, to obtain a particle concentration; measuring an image intensity value of the image data using the data processor; and determining a quality level of the liquid beneficial agent using the particle concentration and the measured image intensity value.

The accompanying figures, where like reference numerals refer to identical or functionally similar elements throughout the separate views, further illustrate various embodiments and explain various principles and advantages all in accordance with the disclosed subject matter. For purpose of explanation and illustration, and not limitation, exemplary embodiments of systems and methods for detecting particles in a beneficial agent in accordance with the disclosed subject matter are shown in FIGS. 1-14. While the present disclosed subject matter is described with respect to using the systems and methods to detect aggregated proteins in a liquid beneficial agent, for example a TNF inhibitor, one skilled in the art will recognize that the disclosed subject matter is not limited to the illustrative embodiment. For example, the detection method can be used to detect any suitable particles, either visible or subvisible, in a liquid beneficial agent, such as contaminants or other undesired particles. In addition, the components and the method of detecting particles in a liquid beneficial agent are not limited to the illustrative embodiments described or depicted herein.

FIG. 1 is a diagram showing an exemplary method according to the disclosed subject matter. At 100, the device and beneficial agent container are made ready for analysis. Certain additional steps, such as calibrating an image detector to a desired sensitivity, can be performed initially and/or periodically, and repeated when each new type of beneficial agent is to be evaluated. Additional adjustments to the system can include the position of the image detector, the position or configuration of optical elements, the wavelength, intensity, or position of the light source, or other applicable parameters described herein. By contrast, some steps can be performed for each beneficial agent container to be tested, such as physically placing the beneficial agent container into alignment with a light source and an image detector. When the steps to prepare the device and beneficial agent container for analysis are completed, a signal can be provided to the device or to the user to indicate that the system is ready for testing.

At 102 of FIG. 1, at least a portion of the beneficial agent in the container is selectively illuminated. If desired, the entire contents of the container can be analyzed. Illuminating the beneficial agent can include directing a light source at the portion of the beneficial agent to be analyzed.

In accordance with one aspect of the disclosed subject matter, the beneficial agent is illuminated by a thin sheet of illumination. The thin sheet of illumination can be formed by the light source, or by an optical element. Forming a thin sheet of illumination in the beneficial agent can create a substantially planar field of light observable by an image detector, and can enhance contrast of an image obtained of the beneficial agent in the area of the thin sheet of illumination. Enhanced contrast of the image can allow for imaging of particles of submicron dimensions, including detecting particles much smaller than the wavelength of light, using the image analysis techniques described below. In some embodiments, selectively illuminating the beneficial agent can include focusing light through an optical element corresponding to the container. That is, an optical element, such as a cylindrical lens, can be provided between the light source and the syringe to form the thin sheet of illumination, as well as operate in concert with the syringe and the image detector to eliminate distortion caused by the curvature of the syringe wall. For example, the beneficial agent container can have a curvature that distorts the focus of the light through the container. An optical element, such as a lens, having a curvature corresponding to the curvature of the container can be introduced between the light source and the container to offset the curvature of the container and better focus the light through the container.

The light source can be any suitable light source to illuminate the container. For example and without limitation, the light source can be a coherent light source, such as a laser. The light source can be selected to produce light having a particular wavelength. For example and without limitation, the light source can provide light having a wavelength selected from a range of about 200 nm to about 1100 nm for a biologic product Light having a wavelength of about 200 nm to about 400 nm can be suitable for exciting an intrinsic fluorescence of a beneficial agent, as described further below. Light having a wavelength of about 400 nm to about 1100 nm can be suitable to allow for light scattering by the particles, which can then be imaged as described further below.

At 104 of FIG. 1, an image from the illuminated portion of the liquid beneficial agent is obtained. The image obtained can be due to light scattering from particles in the illuminated portion of the beneficial agent. Obtaining an image can include sending a signal to the image detector to capture the image. In some cases, such as if a new type of beneficial agent and/or container is being tested or if the configuration of the detection system has been changed, the image detector can first be calibrated to a predetermined sensitivity and/or with a baseline product of a known quality level. In some embodiments, obtaining an image can include focusing the image at the image detector through an optical element corresponding to the container. For example, the beneficial agent container can have a curvature that distorts the focus of the image detector through the container. Hence, and as previously noted, an optical element, such as a lens, having a curvature corresponding to the curvature of the container can be introduced between the image detector and the container to offset the curvature of the container and provide an image that is substantially free of distortion from the curvature of the container. Further, an optical element, such as a microscope objective lens, optically coupled with the image detector can be used to obtain an image of the beneficial agent with increased resolution. Increased resolution of the image can allow detection of particles in the beneficial agent using the image analysis techniques further described below.

Figure 2A:
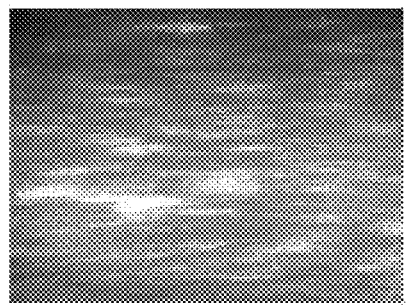
FIGS. 2A-2B are exemplary images illustrating the result of using an optical element to obtain an image in accordance with the disclosed subject matter.
Figure 2B:
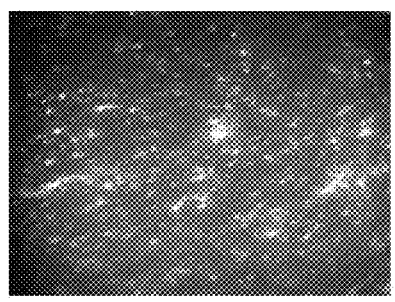

FIGS. 2A and 2B are exemplary images from a beneficial agent obtained by an exemplary image detector 204. FIG. 2A shows an image obtained from a beneficial agent in a pre-filled syringe container 206 without the use of optical elements 208. FIG. 2B shows an image obtained from a beneficial agent in a pre-filled syringe container 206 with the use of optical elements 208, the image being relatively free of distortion compared to the image of FIG. 2A.

For example and without limitation, reference is made to performing the detection method by obtaining a single, still-frame image of the liquid beneficial agent. However, it will be understood that the detection method can be performed by taking a series of still-frame images, a motion video image or photodetector signal of the liquid beneficial agent over a period of time if dynamic analysis is desired. Additionally, while the detection method can be performed using an image of only a select portion of the liquid beneficial agent, the method can likewise be applied to or across the entire contents of the pre-filled syringe container 206. For example, the pre-filled syringe container 206 can be translated across a fixed light in multiple steps to obtain multiple images of the liquid beneficial agent, and/or the light from the light source can be redirected across selected portions of the container to obtain corresponding images. However, reducing the number of image frames obtained and/or reducing the size of the portion of the container to be imaged can increase the throughput, i.e., the number of containers that can be tested in a given time. Hence, high-throughput detection can be performed by utilizing a single frame image of only a portion of the liquid beneficial agent.

Additionally or alternatively, an image from the beneficial agent can be obtained by utilizing an intrinsic fluorescence of the beneficial agent. In certain beneficial agents, for example biologic protein drugs, excitation of intrinsic protein fluorescence due to natural, unmodified amino acids in the beneficial agent can be achieved by illumination of the beneficial agent with light having a wavelength within an absorption band. For example, a wavelength within an absorption band can be within a range of about 200 nm to about 330 nm for certain TNF inhibitors. Excitation of the beneficial agent can cause the beneficial agent to emit fluorescence having an emission wavelength, for example, within a range of about 290 nm to about 500 nm. Other beneficial agents, such as small molecule drugs that are intrinsically fluorescent, can be excited at substantially any suitable ultraviolet, visible, or near-infrared wavelength (for example from about 200 nm to about 900 nm). Hence, an image from the beneficial agent can be obtained by placing an optical filter having a wavelength band corresponding to the emission wavelength of the beneficial agent within the view of the image detector.

Utilizing the intrinsic fluorescence of the beneficial agent to obtain an image can also be incorporated into the system according to the disclosed subject matter to provide calibration and troubleshooting functionality. For example, in addition or as an alternative to the steps described with respect to 100 of FIG. 1, the image of the beneficial agent obtained utilizing the intrinsic fluorescence of the beneficial agent can be obtained initially and/or periodically, or when each new type of beneficial agent is to be evaluated. The image can be analyzed to determine if particles being imaged are indeed protein-containing particles, and not, for example, contaminate particulates, oil droplets, air bubbles, or other undesired non-protein particles. Such undesired particles can be imaged using light scattering, but would not appear in an image obtained utilizing intrinsic fluorescence. If such particles do appear during light scattering, certain parameters of the system can be adjusted, such as the sensitivity or position of the image detector, the position or configuration of the optical elements, the wavelength, intensity, or position of the light source, or any other parameters described herein. Once the system is calibrated utilizing intrinsic fluorescence to confirm that the particles being imaged using light scattering are proteins, detection using light scattering can proceed.

Additionally or alternatively, an image from the beneficial agent can be obtained, using a difference image analysis technique, wherein a difference image can be obtained between two images of the beneficial agent. For example, images of certain samples can have a strong Rayleigh scattering background, which can be caused by a relatively high protein concentration. As such, these images can have a relatively low signal-to-background ratio that can be unsuitable for quantitative detection of particles or aggregates present at low concentrations. The light scattered from concentrated protein monomers can be considered as a steady background image. Accordingly, determining a difference image (or "difference image analysis") can reduce the interfering background to provide an image suitable for quantitative detection of particles or aggregates.

Figure 3A:
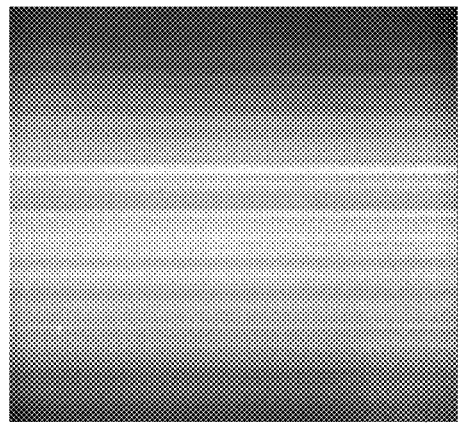
FIGS. 3A-3D are exemplary images illustrating the result of using difference image analysis to obtain an image in accordance with the disclosed subject matter.
Figure 3B:
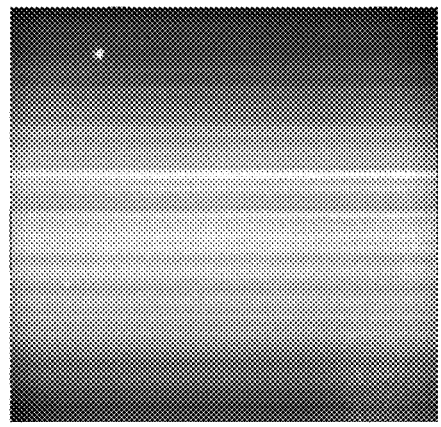
Figure 3C:
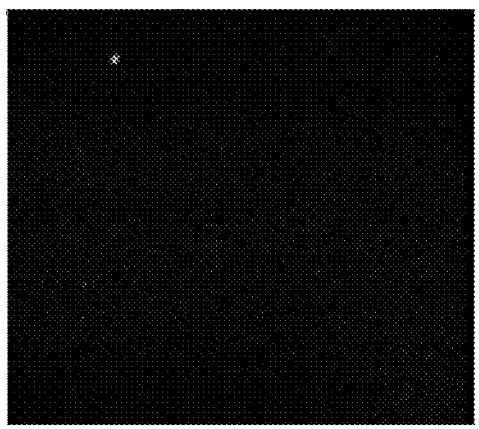
Figure 3D:
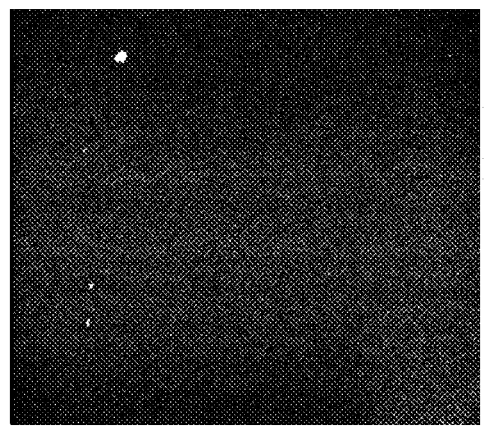

As embodied herein, for purpose of understanding and not limitation, to perform difference image analysis, a first image and a second image of the illuminated portion of the sample can be taken successively. FIG. 3A illustrates an example first image, and FIG. 3B illustrates an example second image. Due at least in part to the movement or diffusion of particles within the sample, particles can appear in different positions in the second image compared to the first image. As such, a difference image can be calculated, for example using ImageJ software available from the National Institutes of Health (NIH), or similar software, to determine a difference between the first image and the second image, and thus reduce the background interference present in the first and second images. An exemplary difference image obtained from the first image and second image is illustrated in FIG. 3C. As shown in FIG. 3C, background interference is reduced, and a number of particles are visible. The black and white contrast of the difference image can be increased to improve the visibility of the particles, as shown for example in FIG. 3D. As such, and as depicted for purpose of illustration herein, performing particle counting on the image of FIG. 3D, as discussed further herein, determines a total of 7 particles in the exemplary difference image, which corresponds to 3.5 particles per image. Using the difference image, the image processing techniques described further herein can be performed, as described further below.

At 106 of FIG. 1, the image obtained at 104 is processed to determine certain characteristics of the image, from which characteristics of the liquid beneficial agent under investigation can be determined. In accordance with the disclosed subject matter, and as embodied herein, two or more image processing techniques are performed independently or in combination on the single image. Combining the two or more image processing techniques thus increases the range and accuracy of particle sizes that can be detected using the detection method. For example and without limitation, and as embodied herein, particles of about 25 nm or greater can be directly identified in the image, and one skilled in the art will recognize that other sizes of particles can be imaged based at least in part on the optical conditions of the system and/or the type of sample being imaged.

The direct imaging technique, such as nanoparticle imaging or other suitable technique, can be performed on the image of the beneficial agent. Direct imaging can be used to obtain a particle concentration. For example and without limitation, the image can be evaluated by counting a number of particles exceeding a size threshold or an intensity threshold to determine a particle concentration. Counting the number of particles exceeding the size threshold or the intensity threshold can be performed using a number of known techniques. For example, particle scattering intensities can be used to estimate particle mass. A particle intensity distribution thus can be generated by identifying the number of particles exceeding a certain predetermined particle scattering intensity and plotting the number of particles over the corresponding image area to obtain a particle concentration. Alternatively, if the number of particles that exceed a predetermined size or intensity is known, then plotting is not required. A variety of suitable algorithms for direct imaging can be used to analyze an image and obtain the particle concentration. For example and without limitation, currently-available software, such as ImageJ, can be utilized to perform these functions. Various tools available through ImageJ, such as "Maximum," "Analyze Particle," and "Histogram," or other suitable software tools can be used to perform particle identification, particle counting, measuring image intensity distributions or the like. Additional tools and software likewise can be used and/or be adapted according to the intended implementation. Accordingly, as will be discussed below, whether and how many particles identified in the image exceed the particle concentration can be used as a factor to determine the quality of the beneficial agent.

Figure 4A:
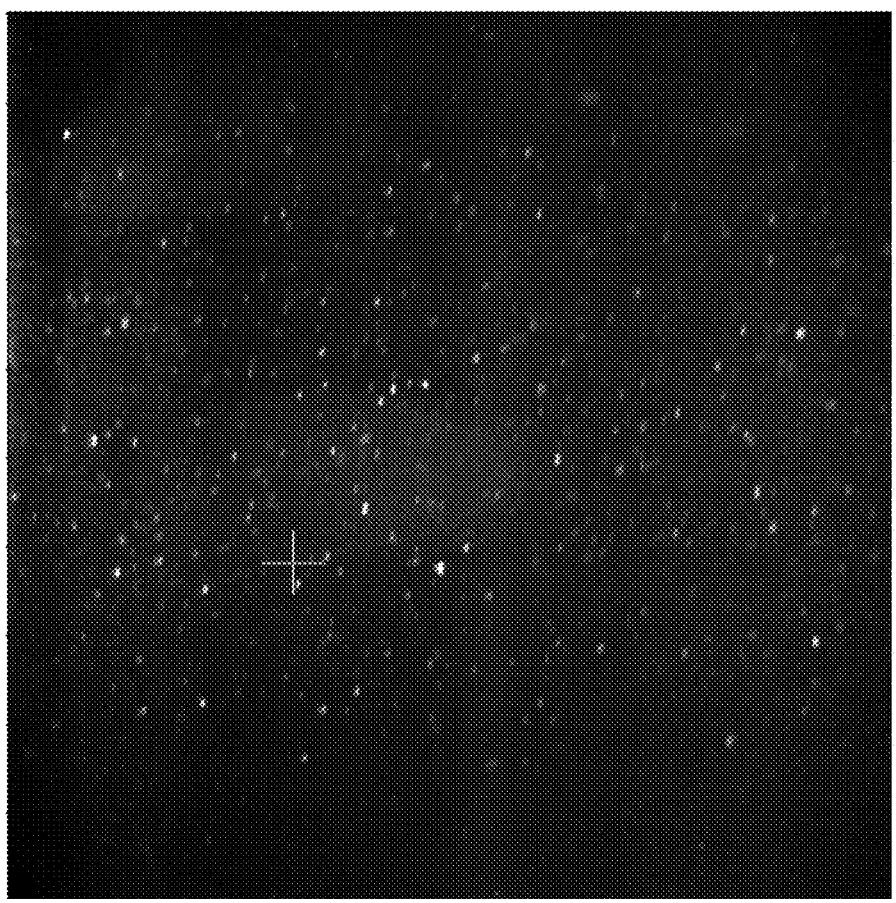
FIGS. 4A-4C are exemplary images illustrating the result of direct imaging in accordance with the disclosed subject matter.
Figure 4B:
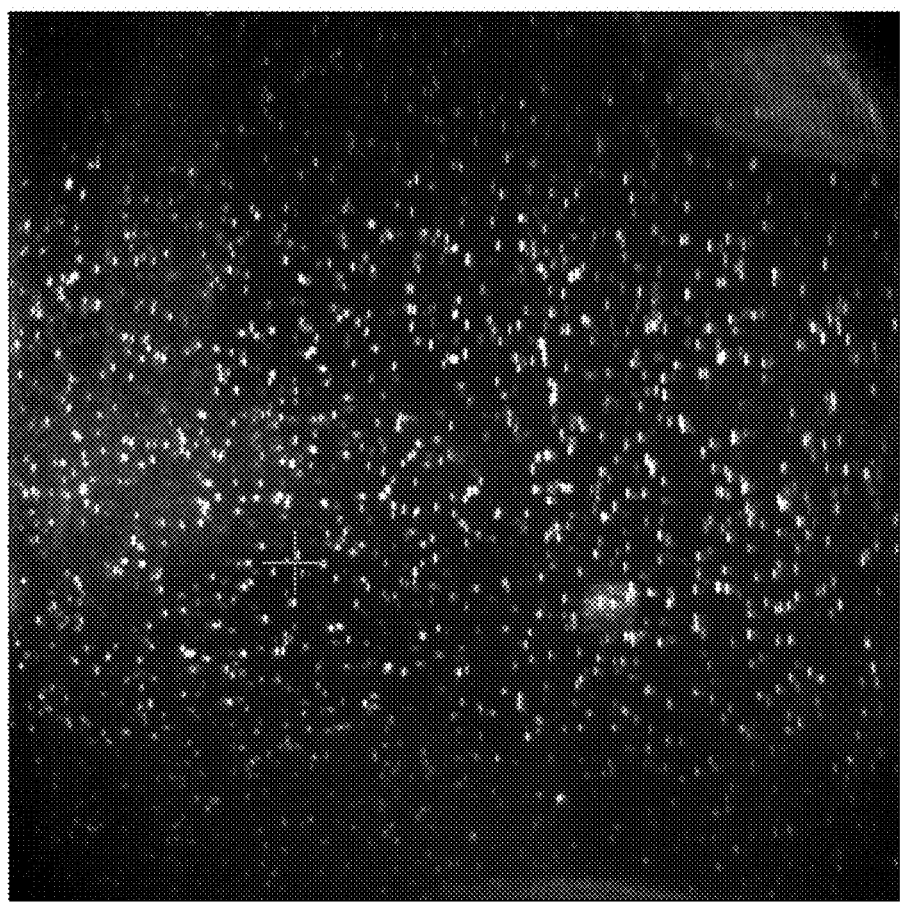
Figure 4C:
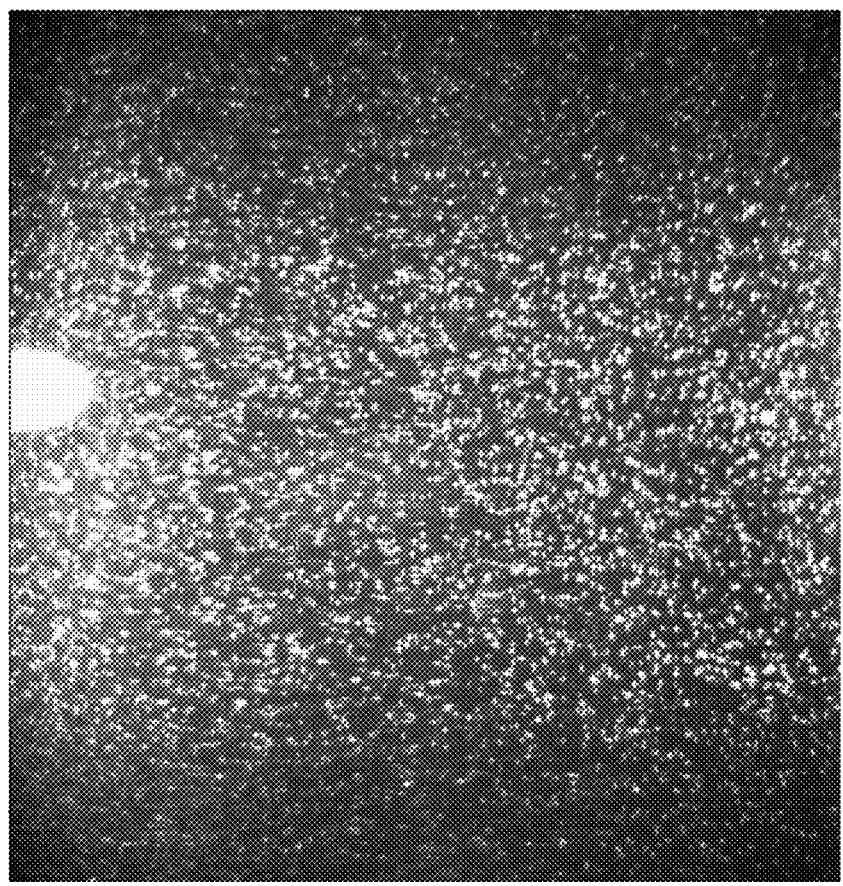

For purpose of illustration and not limitation, FIGS. 4A-4C are exemplary images obtained from a representative image detector of a system according to the disclosed subject matter. FIG. 4A shows an image obtained of 80 nm particles suspended in water. FIG. 4B shows 290 nm particles suspended in water. FIG. 4C shows an image obtained of 500 nm particles suspended in water. The images were obtained under similar conditions of illumination and detection sensitivity. Thus, FIGS. 4A-4C illustrate the performance of the system with respect to direct imaging of sub-micron particles. FIGS. 4A-4C can be analyzed, as described above, by the direct imaging technique to obtain a particle concentration, for example by counting a number of particles exceeding a size threshold or an intensity threshold.

Furthermore, for a sample considered to have a spatially uniform concentration, the particle concentration (i.e., the number of particles per unit volume) can be deduced from an analysis of the number of particles from the measured region of the solution, as described herein. The particle number in one image can thus be considered to be equal to the particle number in the detection volume, and the detection volume can be estimated from the illumination volume. For example, if an illumination area shown in the image is 2 mm by 2 mm, and the thickness of the beam is 0.1 mm, the illumination volume can be determined to be 0.4 microliters. As an additional and confirmatory technique of calibration, a standard solution with known particle concentration can be used, for example and as embodied herein, 490 nm polystyrene particles in water. Alternatively, for solutions that are not considered to be spatially uniform (i.e. spatially non-uniform concentration), it can be beneficial or even necessary to scan the entire solution.

The total particle number in a container ($N_{total}$) can be determined by the relation, $$N_{total} = \frac{N_{per\_image} V_{total}}{V_{detection}}, \quad (1)$$

where $N_{per\_image}$ represents the total number of particles in the image, $V_{total}$ represents the total volume of the container and $V_{detection}$ represents the volume imaged in a single image.

Figure 5A:
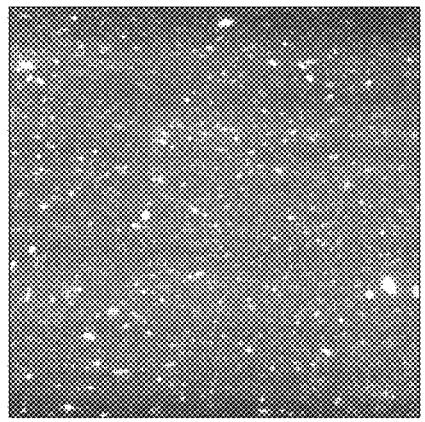
FIGS. 5A-5D are exemplary images illustrating evaluating a sample by particle counting in accordance with the disclosed subject matter.
Figure 5B:
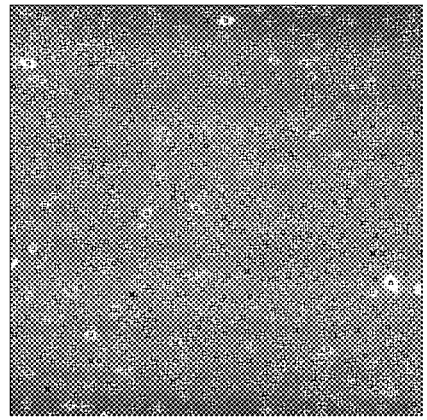
Figure 5C:
Figure 5D:
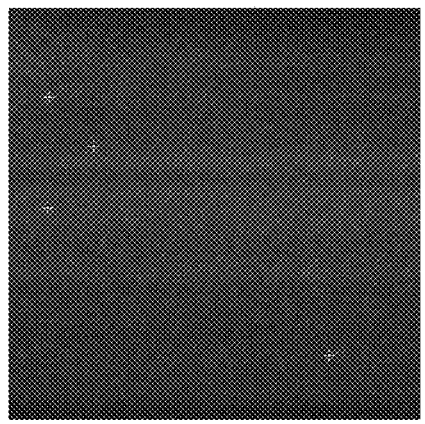

For purpose of illustration and understanding, FIGS. 5A-5D are exemplary images illustrating evaluating a sample by determining a particle concentration or "particle counting" according to the disclosed subject matter. FIG. 5A shows an image obtained of a sample containing 25 mg/ml of bovine serum albumin (BSA) prepared from a powder and without any filtration. FIG. 5C shows an image obtained of a sample containing 25 mg/ml of BSA that was filtered with a 0.2 micron filter. The illumination volume for each image was determined to be 0.25 microliters (0.00025 mL), as described above. Particle counting was performed using ImageJ on each of the images of FIGS. 5A and 5C to determine a particle concentration. FIG. 5B illustrates the result of the particle counting of the image of FIG. 5A. As shown in FIG. 5B, 1023 particles were detected in the image, which corresponds to a particle concentration of about 4.1 million particles per mL (1023 particles/0.00025 mL=4.092 million particles/mL). By comparison, as shown in FIG. 5D, 4 particles were detected in the image of FIG. 5B, which corresponds to a particle concentration of about 16,000 particles per mL (4 particles/0.00025 mL=16,000 particles/mL).

A user can establish a threshold of particle concentration based on a desired quality of a particular sample to be measured. A sample having a particle concentration exceeding the threshold can be determined to be "unacceptable," and thus no further testing of the unacceptable sample need be performed. A sample having a particle concentration that does not exceed the threshold can be subjected to further analysis by determining a total image intensity, from which an average molecular weight can be determined, as described herein. As such, the presence of very small aggregates or particles (for example and as embodied herein, less than about 100 nm), which can be too small to be imaged as discrete particles and thus too small to be counted by particle counting, can still be detected by the subsequent technique.

Separately, a total image intensity analysis can be performed to determine a total image intensity, from which an average molecular mass of particles in the beneficial agent can be determined. The total image intensity analysis can be based on static light scattering (SLS), which can be considered as an indirect imaging technique, and can allow for detection of particles as small as about 10 nm or less. SLS-based indirect imaging can include measuring an image intensity value of the image data. The total image intensity value can be measured, for example, by determining or obtaining a pixel intensity value of each pixel representing the image, or a region of the image of interest, and combining the pixel intensity values obtained to determine the total image intensity value. The total image intensity value can be divided by the number of pixels to obtain an average image intensity value for the image. A variety of suitable algorithms can be used to measure an image intensity value from image data. For example and without limitation, currently-available software, such as ImageJ by the National Institutes of Health described above, can be used to perform these functions. The image intensity value can be considered to be proportional to the average molecular mass and particle concentration of the particles, including molecules, in the measured region, offset by a background intensity.

Figure 6A:
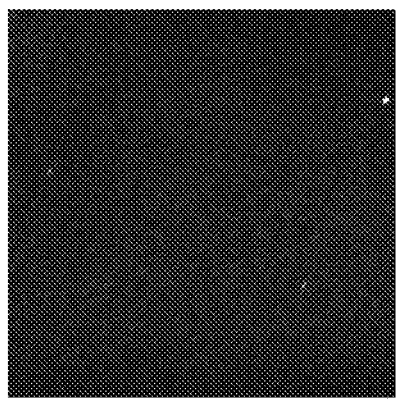
FIGS. 6A-6D are exemplary images illustrating the result of indirect imaging in accordance with the disclosed subject matter.
Figure 6B:
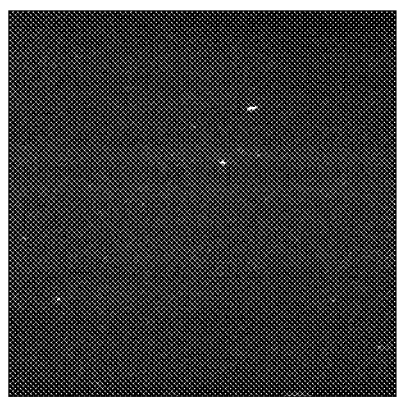
Figure 6C:
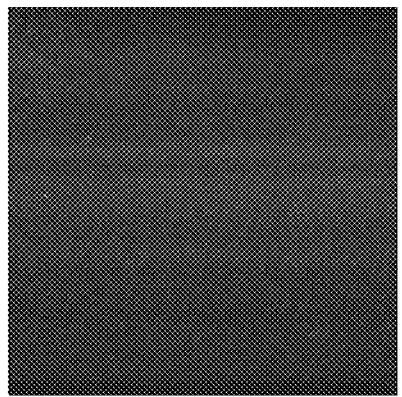
Figure 6D:
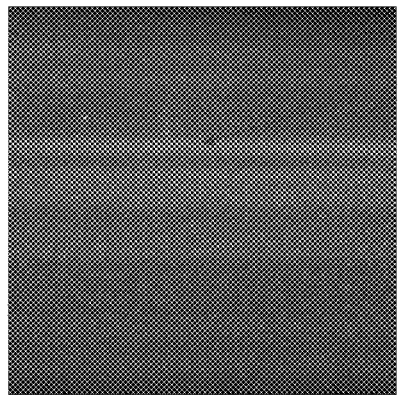

For purpose of illustration and understanding, FIGS. 6A-6D are exemplary images obtained from a representative image detector of a system according to the disclosed subject matter. FIG. 6A shows an image obtained of Milli-Q water in a syringe, which can be representative of a background intensity. FIGS. 6B-6D each shows an image of BSA in a syringe at different concentrations, i.e., 12.5 mg/mL, 25 mg/mL and 50 mg/mL, respectively.

FIGS. 6A-6D illustrate the performance of the system with respect to indirect imaging of particles that are too small to be detected using direct imaging. In FIGS. 6B-6D, for purpose of illustration, a negligible number of particles are observable since any BSA monomers and low molecular weight aggregates, which represent substantially the mass of the sample, are too small to be imaged directly. However, and unlike a conventional system, the system disclosed herein can detect the presence of the BSA since the SLS-intensity (i.e., the total image intensity or the average image intensity) exceeds the background intensity of FIG. 6A.

Figure 7:
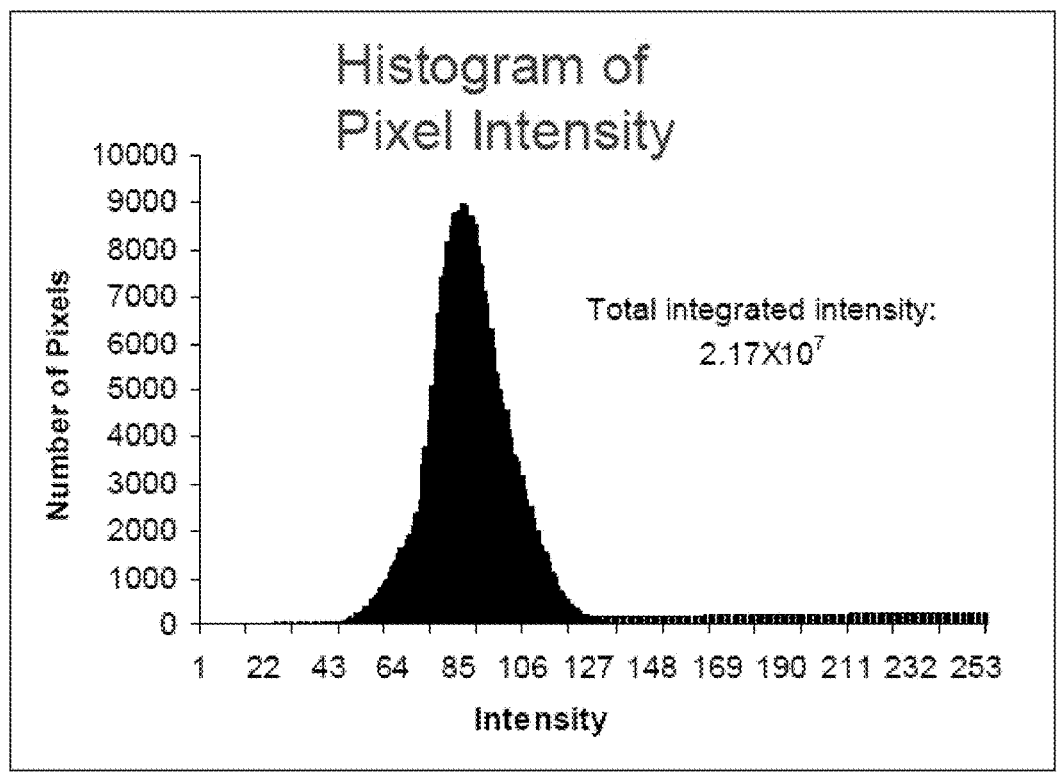
FIG. 7 is an exemplary graph illustrating determining an image intensity in accordance with the disclosed subject matter.

Furthermore, the total image intensity can be determined by measuring an intensity of each pixel in an image, for example by using ImageJ or similar software. The intensity of each pixel can be represented in a histogram. For example, FIG. 7 is a histogram illustrating the intensity of each pixel of the sample of FIG. 6D having 50 mg/mL BSA. The total image intensity can be determined, for example, by integrating (i.e., finding the area under) the plot of the intensity of each pixel in FIG. 7. For example, as shown in FIG. 7, the total image intensity (or "total integrated intensity") is determined to be $2.17 \times 10^7$.

Based upon the above, the image intensity value and particle concentration can be used to determine an average molecular weight of the particles in the sample, and as such can be used as a factor to determine the quality of the beneficial agent. For example, and for purpose of understanding and not limitation, under Rayleigh scattering conditions, the image intensity value ($I_{Total}$) can be considered linearly proportional to the average molecular weight ($M_W$) and concentration (C), offset by a background intensity ($I_{background}$), as represented by, $$I_{Total} = B_{constant} M_w C + I_{background}.\qquad(2)$$

As such, with a sample including a protein of known molecular weight and independently determined concentration, the instrument constant ($B_{constant}$) can be determined, and the system can be calibrated for average molecular weight detection using eq. (2) above. The background intensity can be measured with a baseline solution, for example a solution of pure water or buffer without protein. Further details of static light scattering techniques to characterize molecules, and related aspects of physical chemistry as known in the art, can be relied upon for further understanding and modification of the disclosed subject matter.

Figure 8:
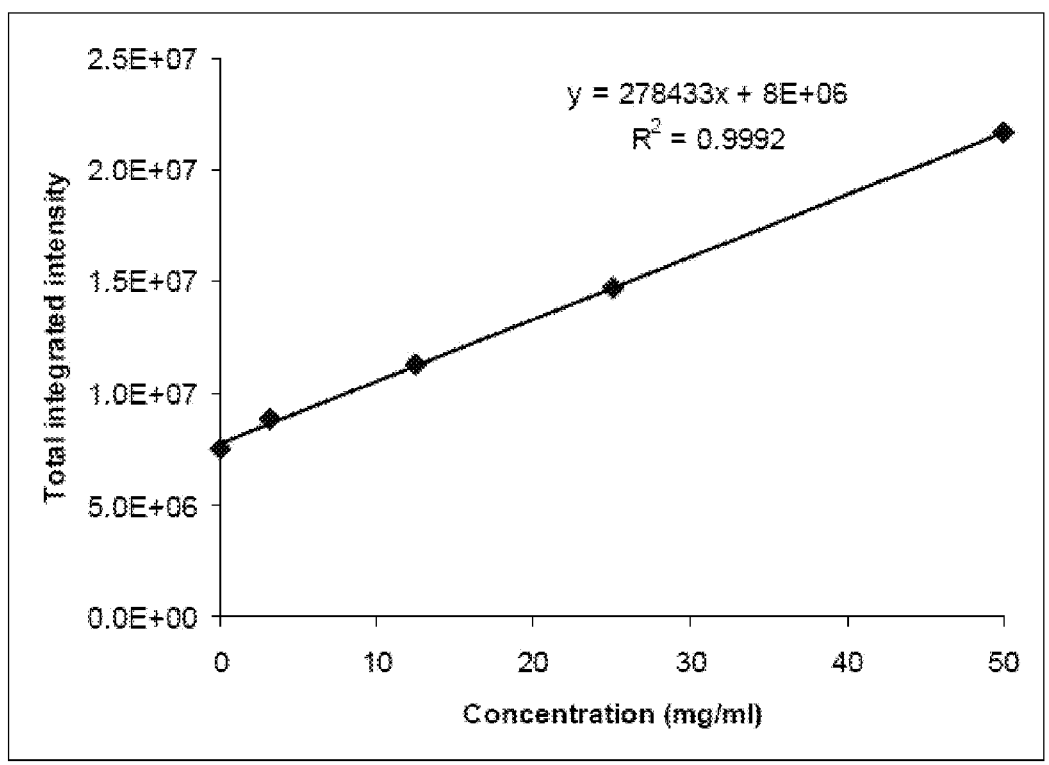
FIG. 8 is an exemplary graph illustrating the relationship between image intensity and concentration in accordance with the disclosed subject matter.

FIG. 8 is a diagram illustrating the total image intensity of each sample having different concentrations of BSA. As shown in FIG. 8, for purpose of illustration and not limitation, the total image intensity has a linear relationship to particle concentration. FIG. 8 illustrates that the technique according to the disclosed subject matter can quantitatively detect variations in concentration of a moderately sized protein (i.e., BSA having a molecular weight of about 67 kD) down to less than 5 mg/mL. As such, the technique according to the disclosed subject matter can be applied to biologic beneficial agents, which can typically have a molecular weight of about 150 kD, even at low concentrations.

Figure 9A:
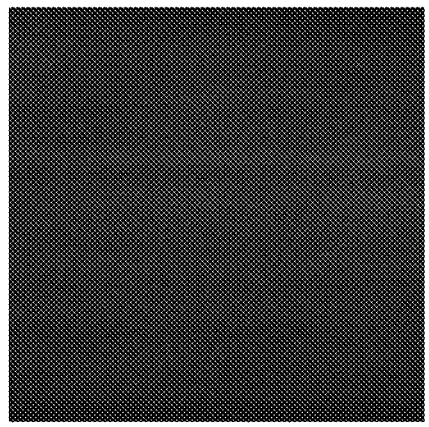
FIGS. 9A-9B are exemplary images illustrating the result of indirect imaging on an untreated sample and a heat-treated sample, respectively, for purpose of comparison.
Figure 9B:
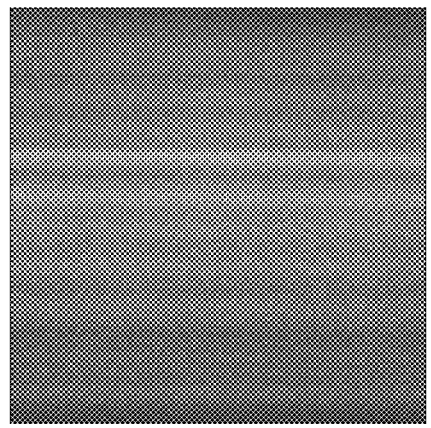
Figure 10:
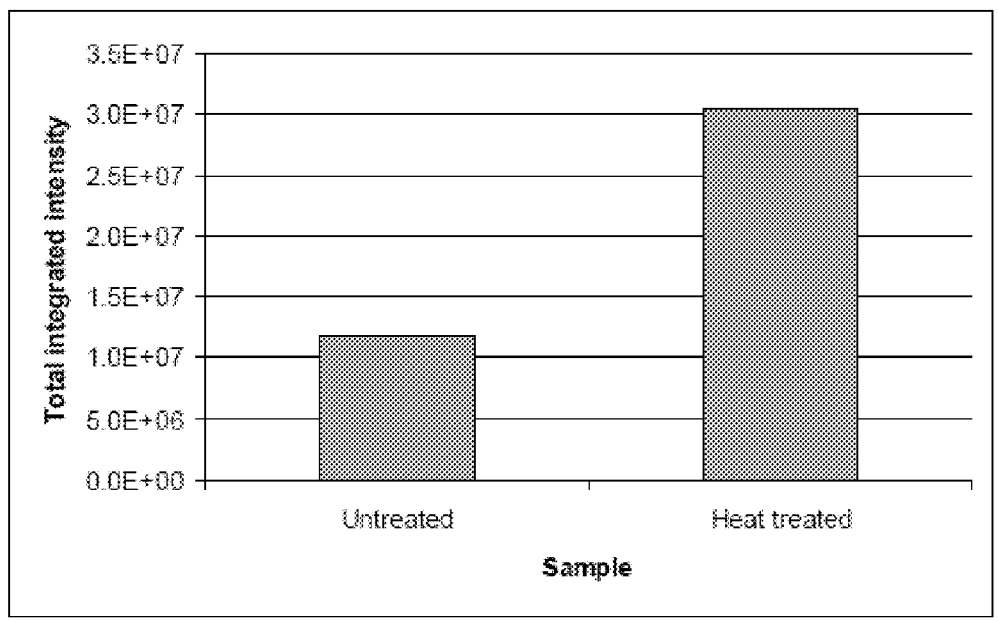
FIG. 10 is an exemplary graph illustrating the image intensity of the samples of FIGS. 9A-9B, for purpose of comparison.

To further illustrate the effectiveness of the system disclosed herein, without limitation, a sample having a 12.5 mg/mL concentration of BSA, was heated to 65° C. for one minute to cause some degree of denaturation and aggregation. FIGS. 9A-9B illustrate images of the sample of the untreated sample (FIG. 9A) and the heat-treated sample (FIG. 9B), respectively, for purpose of comparison. Comparing the samples of FIGS. 9A-9B, naked eye inspection of the syringes did not show an apparent difference between the samples. Furthermore, particle counting did not measure a detectable difference in aggregates caused by heating the sample. However, by obtaining the average image intensity value using the SLS-based measuring technique, even in the absence of resolvable particles, the diffuse white sheen across the image in FIG. 9B yields a total image intensity of about $3.1 \times 10^7$. FIG. 10 illustrates the total image intensity of the untreated sample of FIG. 9A compared to the heat-treated sample of FIG. 9B. The heat-treated sample was measured to have approximately a 5.6-fold increase in total image intensity over the untreated sample of FIG. 9A, after subtracting the background scattering obtained from FIG. 6A. Based on an average molecular weight of untreated BSA of 72.6 kD (assuming a 10% dimer content of a typical commercial product), the result illustrates that the average molecular weight of the heat-treated sample has increased to 403.7 kD. Thus, the degree of denaturation and/or aggregation caused by heating sample FIG. 9A can be shown.

Figure 11:
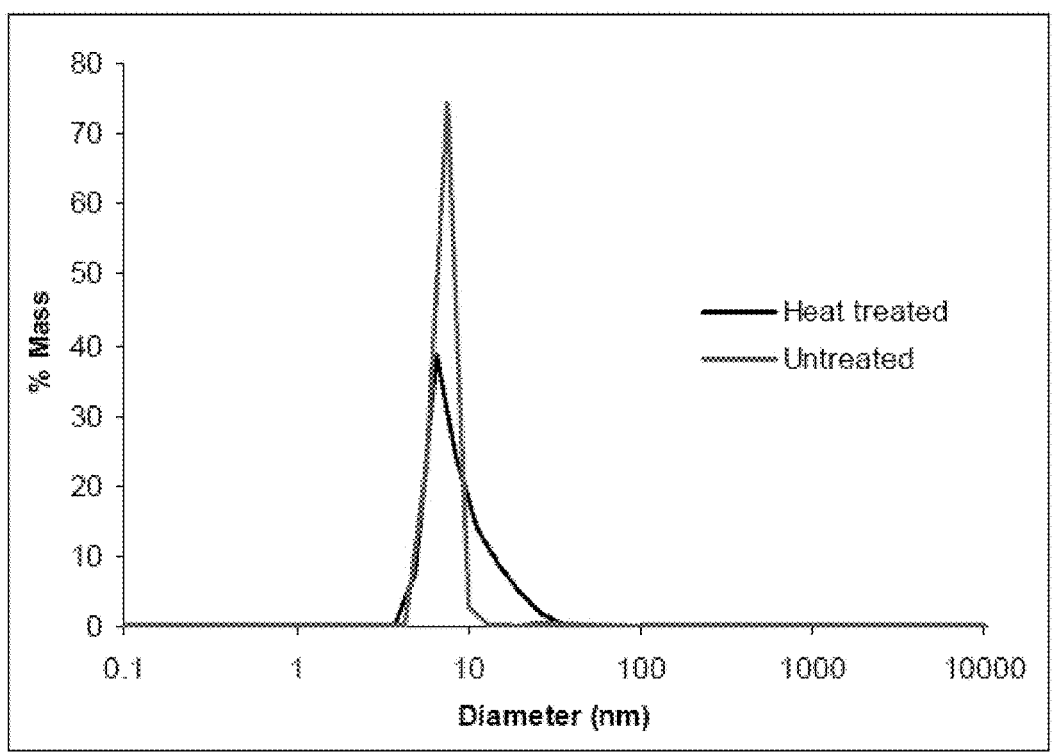
FIG. 11 is a representative graph of the samples of FIGS. 9A-9B obtained using a dynamic light scattering technique for purpose of comparison.

To further demonstrate the benefit of the methods and systems disclosed herein, and merely for purpose of comparison, FIG. 11 is a diagram illustrating a mass-weighted molecular size distribution obtained by an offline DLS-based analysis of the same samples imaged in FIGS. 9A and 9B. FIG. 11 illustrates that the heat treatment caused an increase in small-sized aggregates (i.e., less than 35 nm for this sample).

Furthermore, it is noted for purpose of explanation that the intrinsic molecular particle size distribution of the BSA solution of FIG. 9A is slightly heterogeneous, and thus the mass-weighted particle size distribution shown in FIG. 11 is centered around 7 nm diameter, with slight broadness. After the heat treatment of the sample resulting in the FIG. 9B image, DLS analysis ascertains a significantly perturbed sample consisting of the native monomer (at about 7 nm) plus smaller aggregates. As such, the bulk of these smaller aggregates are too small to be detected as distinct "particles" in the direct imaging mode, but can be detected by the SLS-based indirect imaging analysis of the disclosed method and system.

Figure 12:
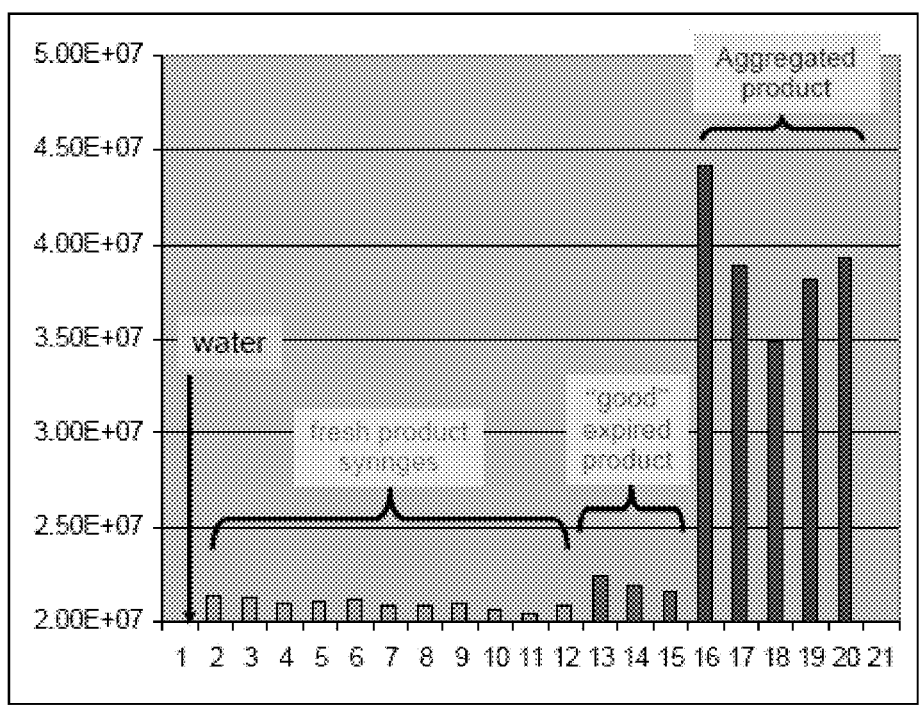
FIG. 12 is an exemplary diagram illustrating exemplary results of indirect imaging analysis on multiple samples for purpose of comparison.

With reference to FIG. 12, a diagram is provided showing exemplary results of SLS-based indirect imaging analysis performed on images of 20 different pre-filled syringes. The vertical axis represents static light scattering total intensity values measured by summing the intensities of all pixels of each image. Sample 1 shows a total intensity value for an image from a syringe filled with water. Samples 2-12 show a total intensity value for images from syringes containing a fresh beneficial agent of known and acceptable quality level. Such data can be used for purpose of calibration of the system for determination of acceptable quality level, as described further below. Samples 13-15 show intensity values for images from syringes containing beneficial agents of extended shelf-life but determined to be within acceptable quality level based upon the method and system herein. Samples 16-20 show intensity values for images of beneficial agents of extended shelf life but determined to have an unacceptable amount of aggregated proteins.

At 108 of FIG. 1, the results of the two or more image processing techniques performed in 106 are evaluated to determine a quality level of the liquid beneficial agent. The determination of the quality level can be based independently on each of the results obtained by the image processing techniques performed in 106. For example, the particle concentration obtained from the direct imaging technique can be compared to a particle concentration threshold. If the particle concentration exceeds the particle concentration threshold, the quality of the liquid beneficial agent can be considered to be unacceptable, and a warning can be generated that the liquid beneficial agent has failed the inspection (at 110).

Separately, the image intensity value (total or average) measured using the indirect imaging technique can be compared to an image intensity threshold. If the image intensity value exceeds the image intensity threshold, then the quality of the liquid beneficial agent can be considered to be unacceptable, and a warning can be generated that the liquid beneficial agent has failed the inspection (at 110). Alternatively, the average molecular mass can be calculated from the image intensity value, and the average molecular mass can be compared to an average molecular mass threshold to determine the quality of the liquid beneficial agent.

The method and system disclosed herein therefore can be used to confirm and/or determine acceptable quality levels of a beneficial agent in individual containers at a high-throughput rate. For example, if all the results of the image processing are evaluated and none of the results exceed predetermined threshold values, then the beneficial agent can be considered to be acceptable. An indication can be generated that the liquid beneficial agent has passed the inspection (at 112) and/or a new beneficial agent can be made ready for inspection using the detection method.

Alternatively, or additionally, and in accordance with another aspect of the disclosed subject matter, the quality level can be a function of the results of the image processing techniques in combination. A representative profile can relate the results obtained by the image processing techniques to the quality level of the beneficial agent. The representative profile embodied herein can contain the particle concentration threshold and the total intensity threshold that, if exceeded, indicate that the beneficial agent is unacceptable and does not pass inspection. The representative profile, and thus the particle concentration threshold and the total intensity threshold, can be based on a variety of factors, including but not limited to the type of beneficial agent being inspected, the concentration of the beneficial agent being inspected, and the optical configuration of the detection system.

In accordance with another aspect of the disclosed subject matter, a system is provided for detection of particles in a liquid beneficial agent contained within a container (also referred to herein as a "detection system"). The system includes a light source configured to illuminate at least a portion of the container; an image detector configured to obtain an image of the liquid beneficial agent in the illuminated portion of the container; and a data processor coupled to the image detector and programmed to analyze image data representing the image from the image detector to obtain a particle concentration, measure a total image intensity value of the image data, and determine a quality level of the liquid beneficial agent using the data processor based on the particle concentration and the measured total image intensity value.

Figure 13:
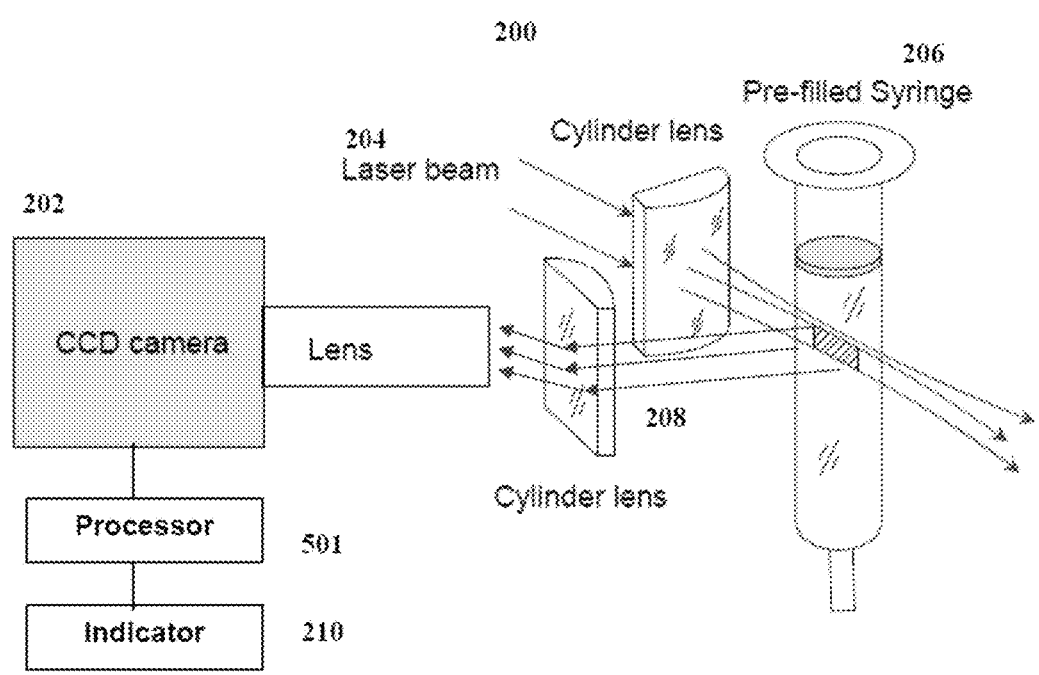
FIG. 13 is a diagram illustrating a representative system for use with the method of FIG. 1 according to an illustrative embodiment of the disclosed subject matter.
Figure 14:
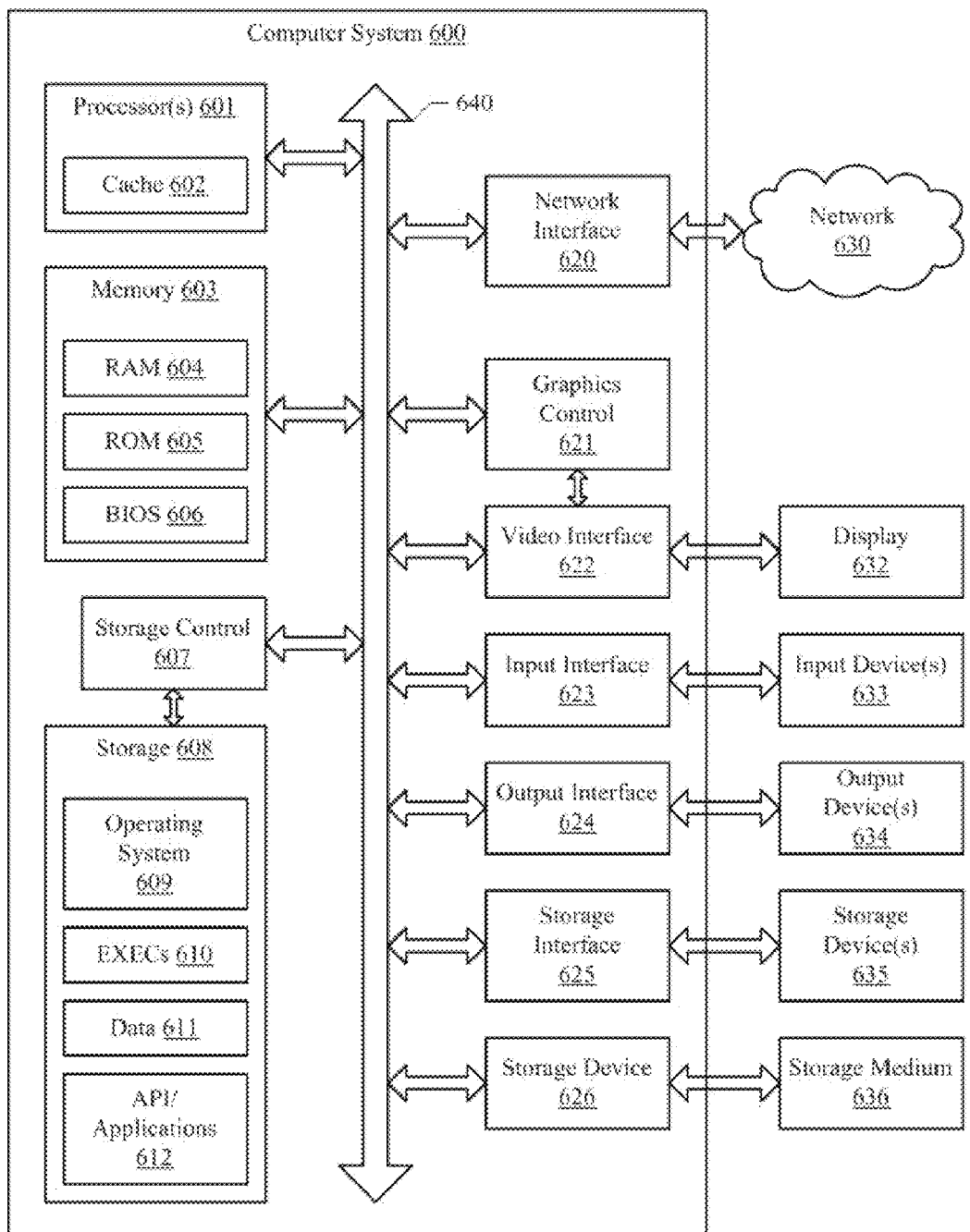
FIG. 14 is an exemplary diagram illustrating further details of a system for use with the method of FIG. 1.

For purpose of illustration and not limitation, FIG. 13 is a diagram schematically depicting an exemplary detection system 200 for use with the detection method described herein. An exemplary container 206 is shown, embodied as a pre-filled syringe, however the container can be any suitable container 206 for containing a liquid beneficial agent, including but not limited to a glass vial, quartz cell, or any other container suitable for optical spectroscopy applications. An exemplary light 204 is shown, embodied as a laser beam. However, the light 204 can be any suitable light for selectively illuminating at least a portion of the container, including but not limited to a standard light bulb and a fluorescent lamp. For example and not limitation, a light source used to produce light 204 in an exemplary detection system 200 is LaserMax® 647 nm diode laser. An exemplary image detector 202 is shown, embodied as a CCD camera and lens, however the image detector 202 can be any suitable image detector for obtaining an image and providing image data. For example and not limitation, an image detector 202 used in an exemplary detection system 200 is an Optronics® QPX-285C Digital Microscope Camera with an Olympus® 10× objective lens. Exemplary optical elements 208 are shown, embodied as cylindrical lenses, however the optical elements 208 are optional and can correspond to the shape of container 206 to permit the capture of an undistorted image. For example and not limitation, exemplary optical elements 208 used to focus the image detector 202 and light 204 in an exemplary detection system 200 are Edmund Optics® cylinder lenses having a focal length of 50 nm. An exemplary processor 601 is shown, which is embodied as a component of the computer system architecture 600, as shown in FIG. 14. For example and not limitation, an exemplary processor 601 is an Intel Pentium 4®.

As an example and not by limitation, as shown in FIG. 14, the computer system having architecture 600 can provide functionality as a result of processor(s) 601 executing software embodied in one or more tangible, computer-readable media, such as memory 603. The software implementing various embodiments of the present disclosure can be stored in memory 603 and executed by processor(s) 601. A computer-readable medium can include one or more memory devices, according to particular needs. Memory 603 can read the software from one or more other computer-readable media, such as mass storage device(s) 635 or from one or more other sources via communication interface. The software can cause processor(s) 601 to execute particular processes or particular parts of particular processes described herein, including defining data structures stored in memory 603 and modifying such data structures according to the processes defined by the software. An exemplary input device 633 can be, for example, the imaging device 202 coupled to the input interface 623 to provide image data to the processor 601. An exemplary output device 634 can be, for example, an indicator 210, such as an LED light, coupled to the output interface 623 to allow the processor 601 to provide an indication to the user that a beneficial agent sample is acceptable or unacceptable. Additionally or alternatively, the computer system 600 can provide an indication to the user by sending text or graphical data to a display 632 coupled to a video interface 622. Furthermore, any of the above components can provide data to or receive data from the processor 601 via a computer network 630 coupled the network interface 620 of the computer system 600. In addition or as an alternative, the computer system can provide functionality as a result of logic hardwired or otherwise embodied in a circuit, which can operate in place of or together with software to execute particular processes or particular parts of particular processes described herein. Reference to software can encompass logic, and vice versa, where appropriate. Reference to a computer-readable media can encompass a circuit (such as an integrated circuit (IC)) storing software for execution, a circuit embodying logic for execution, or both, where appropriate. The present disclosure encompasses any suitable combination of hardware and software.

The systems and methods provided herein can be utilized to inspect a variety of liquid beneficial agents, including but not limited to small molecule pharmaceuticals and large molecule biologics. For example, proteins having a protein concentration between about 0.1 mg/ml and about 200 mg/ml can be inspected. Proteins inspected using the systems and methods provided herein can be, including but not limited to, fusion proteins, antibodies, and any other suitable proteins. An exemplary antibody inspected using the systems and methods provided herein is an anti-Tumor Necrosis Factor alpha (TNFα) antibody, or antigen-binding fragment thereof.

The systems and methods provided herein can be utilized to ensure that a beneficial agent product has a predetermined quality level. The quality level can be related to the amount and/or size of aggregates, contaminants, or other particles in the beneficial agent. By using the method and system disclosed herein, this determination can be made at the time and site of manufacture, packaging, or even shipment. Additionally, or alternatively, individual inspections can be performed by the pharmacist, physician, and/or use if a suitable beneficial treatment product is available in accordance with the disclosed subject matter. Such a beneficial treatment product includes a container containing a liquid beneficial agent; a light source configured to illuminate at least a portion of the container; an image detector configured to obtain an image of the liquid beneficial agent in the illuminated portion of the container; and a data processor coupled to the image detector. The data processor is programmed to analyze image data representing the image from the image detector to obtain a particle concentration, measure a total image intensity value of the image data, and determine a quality level of the liquid beneficial agent using the data processor based on the particle concentration and the measured total image intensity value.

While the disclosed subject matter is described herein in terms of certain preferred embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

We claim:
1. A method for inspecting a liquid beneficial agent contained within a container, comprising:
   selectively illuminating at least a portion of the liquid beneficial agent having protein particles therein;
   obtaining an image from the illuminated portion of the liquid beneficial agent;
   analyzing image data representing the image, using a data processor, to identify a number of particles having a size greater than or equal to a particle size threshold to thereby obtain a particle concentration, wherein the particle size threshold represents the size at or above which particles can be counted by the data processor;
   measuring an image intensity value of the image data, using the data processor, to detect particles having a size less than the particle size threshold, including determining a pixel intensity value of each pixel of a plurality of pixels of the image data and combining the pixel intensity values of the plurality of pixels to thereby determine the image intensity value;
   determining a quality level of the liquid beneficial agent, using the data processor, by calculating an average molecular mass of the particles, wherein the average molecular mass is linearly proportional to the measured image intensity value and the particle concentration; and
   packaging the liquid beneficial agent if the quality level is within a predetermined quality level range.

2. The method according to claim 1, wherein selectively illuminating the portion of the liquid beneficial agent comprises focusing light through an optical element corresponding to the container to provide an undistorted image of the liquid beneficial agent.

3. The method according to claim 1, wherein the liquid beneficial agent is selectively illuminated with light having a wavelength in a range from about 200 nm to about 1100 nm.

4. The method according to claim 1, wherein the image is obtained by light scattering from particles in the illuminated portion of the liquid beneficial agent.

5. The method according to claim 1, wherein the liquid beneficial agent has intrinsic fluorescence and the beneficial agent is selectively illuminated with light having an excitation wavelength suitable to cause the liquid beneficial agent to emit fluorescent light of an emission wavelength.

6. The method according to claim 5, wherein obtaining the image comprises using an optical filter corresponding to the emission wavelength of the emitted fluorescent light.

7. The method according to claim 1, wherein obtaining the image comprises focusing the image at an image detector through an optical element corresponding to the container to provide an undistorted image from the liquid beneficial agent.

8. The method according to claim 1, wherein obtaining the image comprises:
   capturing a first image and a second image from the illuminated portion of the liquid beneficial agent; and
   using difference image analysis on the first image and the second image to obtain the image.

9. The method according to claim 1, further comprising calibrating an image detector to a predetermined sensitivity.

10. The method according to claim 1, wherein analyzing the image data to obtain the particle concentration is performed using a single image frame.

11. The method of claim 1, wherein obtaining the particle concentration comprises counting a number of particles exceeding the particle size threshold to generate a particle size distribution.

12. The method of claim 11, wherein counting a number of particles exceeding the particle size threshold comprises measuring particle scattering intensities to estimate the particle size distribution.

13. The method according to claim 1, wherein determining the quality of the liquid beneficial agent further comprises comparing the particle concentration to a particle concentration threshold.

14. The method according to claim 13, wherein determining the quality of the liquid beneficial agent further comprises comparing the image intensity value to an image intensity threshold.

15. The method according to claim 1, wherein the average molecular mass of the particles is calculated by reducing the image intensity value by an intensity background value to obtain a reduced image intensity value, and dividing the reduced image intensity value by an instrument constant and the particle concentration.

16. The method according to claim 1, further comprising providing an indication to a user that the liquid beneficial agent is acceptable if the quality level is within a predetermined quality level range.

\* \* \* \* \*